United States Patent [19]

Shibayama et al.

[11] Patent Number: 4,675,391
[45] Date of Patent: Jun. 23, 1987

[54] GLYCOSIDE DERIVATIVES

[75] Inventors: Shohei Shibayama; Yuzi Matsuzaki, both of Tokorozawa; Shoji Yoshimura, Iruma; Masayoshi Ito, Kunitachi; Yoshiyasu Shitori, Tokyo; Tomoya Ogawa, Musashino, all of Japan

[73] Assignee: Kanto Ishi Pharmaceutical Co., Ltd., Tokyo, Japan

[21] Appl. No.: 832,374

[22] Filed: Feb. 24, 1986

[30] Foreign Application Priority Data

Mar. 6, 1985 [JP] Japan .................................. 60-43970

[51] Int. Cl.$^4$ ............................................ C07H 15/00
[52] U.S. Cl. .................................... 536/17.4; 536/18.4
[58] Field of Search ................. 536/18.4, 17.4; 514/25

[56] References Cited

U.S. PATENT DOCUMENTS 4,248,999 2/1981 Baba et al. ......................... 536/17.4

FOREIGN PATENT DOCUMENTS 0181295 10/1985 Japan .................................. 536/18.4

OTHER PUBLICATIONS

Chem. Bor.: 99, 611–617 (1966).
Can J. Chem.: 60, 547–553 (1982).

Primary Examiner—Johnnie R. Brown
Assistant Examiner—Elli Peselev
Attorney, Agent, or Firm—Oblon, Fisher, Spivak, McClelland & Maier

[57] ABSTRACT

This invention provides a novel compound having a formula such as

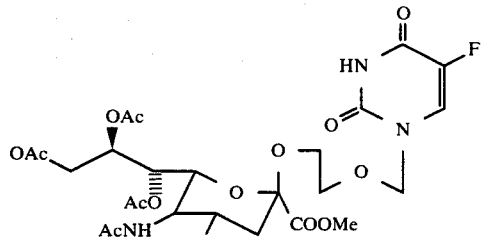

or

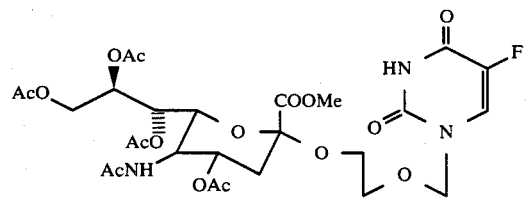

This invention also provides a process for preparing such a compound. The novel compound has excellent immunological activity.

4 Claims, No Drawings

GLYCOSIDE DERIVATIVES

BACKGROUND OF THE INVENTION

(1) Field of the Invention

The present invention relates to glycoside having an excellent immunological activity and processes for preparation thereof, particularly to N-acetylneuraminic acid derivatives included in glycoside and process for preparation thereof.

(2) Description of the Prior Art

So far, it has been known in the art that N-substituted neuraminic acid such as N-acetylneuraminic acids and the like are present in many animals and on the cell surface of several bacterias as a complex of sialic acid such as glycoprotein, glycolipid, oligosaccharide or polysaccharide.

Recently, N-substituted neuraminic acids have become important substances in medicine and pharmaceutics relative to nerve function, cancer, inflammation, immunity, viral infection, differentiation, hormone receptor etc and have been noted as unique active molecules located on the cell surface. However, the role of N-substituted neuraminic acids in the complex of sialic acid has not been ascertained yet.

Furthermore, N-substituted neuraminic acids have been studied by many organic chemists and therefore, many kinds of simple derivatives thereof have been obtained. But no derivative having an excellent immunological activity has been obtained yet.

On the other hand, the average span of human life has been extended because of improvements in medical treatment for malignant tumor of hematopoietic organ, many kinds of cancers, and collagen disease. On the other hand, with the great increase in use of medicines, for example, medicines for adrenal cortical hormone or immunosuppressant, a number of undesirable side effects arise together with lowering and decrease in immunological competence.

SUMMARY OF THE INVENTION

Under such circumstances, the inventors of the present invention have paid special attention to sialic acid which is a bio-inherent ingredient and they continued their research on control agents for immunity having few side effects because of its chemical modification and control effects for immunological surveillance. As a result of such research, the inventors have succeeded in finding the novel compounds of the present invention having immunoregulative effect in which suppressor T cell is activated and production of immunoglobulin of B cell is restrained.

The principal object of the present claimed invention is to provide novel compounds having an excellent immunological activity, especially the immunoregulation effect.

Another object of this invention is to provide effective processes for preparing the novel compounds.

These and other objects of this invention are made clear hereunder.

According to the present invention, novel glycoside having the following general formula (I) are provided.

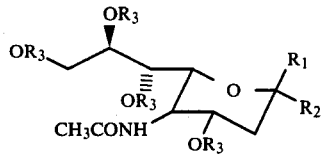

wherein $R_1$ is selected from

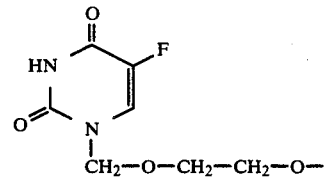

group, alkoxycarbonyl group, carboxyl group and salts of carboxyl group, $R_2$ is alkoxycarbonyl group, carboxyl group or salts of carboxyl group when $R_1$ is

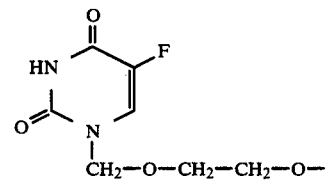

group, $R_2$ is

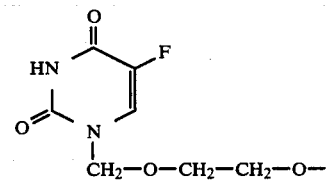

group when $R_1$ is alkoxycarbonyl group, carboxyl group or salt of carboxyl group, and $R_3$ is a hydrogen atom or acetyl group.

The alkoxycarbonyl group of the present invention may be exemplified by methoxycarbonyl group, ethoxycarbonyl group or the like.

The salt of carboxyl group may be exemplified by alkali metal salt or alkali earth metal salt such as sodium salt, potassium salt, calcium salt and the like, of carboxyl group.

The compound (I) of the present invention includes a β configuration derivative (β-derivative) of which $R_1$ is

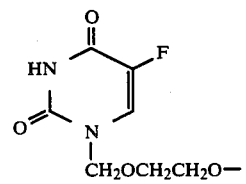

group and a α configuration derivative (α-derivative) of which $R_2$ is

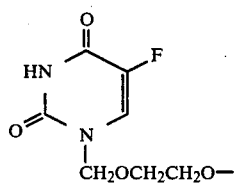

group.

The compound of the present invention represented by the general formula (I) can be prepared by a method shown by the following serial formulas from methyl-2-chloro-4,7,8,9-tetra-0-acetyl-β-D-N-acetylneuraminate (hereinafter compound (II)) and 5-fluoro-1-[(2-hydroxyethoxy)methyl]uracil (hereinafter compound (III)) and obtained as compounds (IV) to (XI). The compounds (IV) to (XI) were named as follows:

compound (IV): 1-0-[methyl(5-N-acetyl-3,5-dideoxy-4,7,8,9-tetra-0-acetyl-β-D-glycero-D-galacto-5-fluoro-1,2,3,4-tetrahydropyrimidin-1-yl)methy]-ethane diol compound (V): 1-0-[methyl(5-N-acetyl-3,5-dideoxy-4,7,8,9-tetra-0-acetyl-α-D-glycero-D-galacto-2-nonulopyranosyl)onate]-2-0[(2,4-dioxo-5-fluoro-1,2,3,4-tetrahydropyrimidin-1-yl)methyl]-ethane diol compound (VI): 1-0-[methyl(5-N-acetyl-3,5-dideoxy-β-D-glycero-D-galacto-2-nonulopyranosyl)onate]-2-0-[(2,4-dioxo-5-fluoro-1,2,3,4-tetrahydropyrimidin-1-yl)methyl]-ethane diol compound (VII): 1-0-[-methyl(5-N-acetyl-3,5-dideoxy-α-D-glycero-D-galacto-2-nonulopyranosyl)onate]-2-0-[(2,4-dioxo-5-fluoro-1,2,3,4-tetrahydropyrimidin-1-yl)methyl]-ethane diol compound (VIII): 1-0-[-sodium(5-N-acetyl-3,5-dideoxy-βD-glycero-D-galacto-2-nonulopyranosyl)onate]-2-0-[(2,4-dioxo-5-fluoro-1,2,3,4-tetrahydropyrimidin-1-yl)methyl]-ethane diol compound (IX): 1-0-[sodium(5-N-acetyl-3,5-dideoxy-αD-glycero-D-galacto-2-nonulopyranosyl)onate]2-0-[2,4-dioxo-5-fluoro-1,2,3,4-tetrahydropyrimidin-1-yl)methyl]-ethane diol compound (X): 1-0-[(5-N-acetyl-3,5-dideoxy-β-D-glycero-D-galacto-2 nonulopyranosyl)onic acid]-2-0-[(2,4-dioxo-5-fluoro-1,2,3,4-tetrahydropyrimidin-1-yl)methyl]-ethane diol compound (XI): 1-0-[(5-N-acetyl-3,5-dideoxy-α-D-glycero-D-galacto-2-nonulopyranosyl)onic acid]-2-0-[(2,4-dioxo-5-fluoro-1,2,3,4 -tetra-hydropyrimidin-1-yl)methyl]-ethane diol

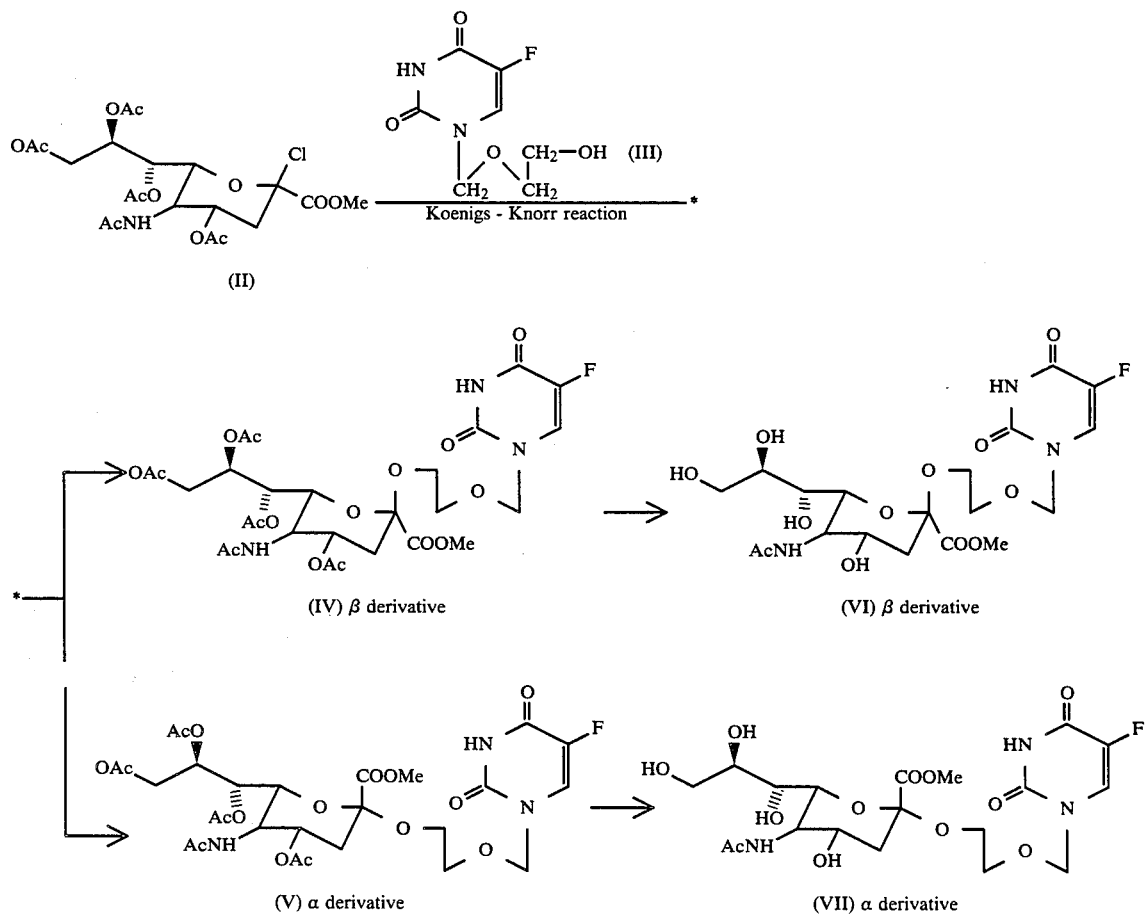

-continued

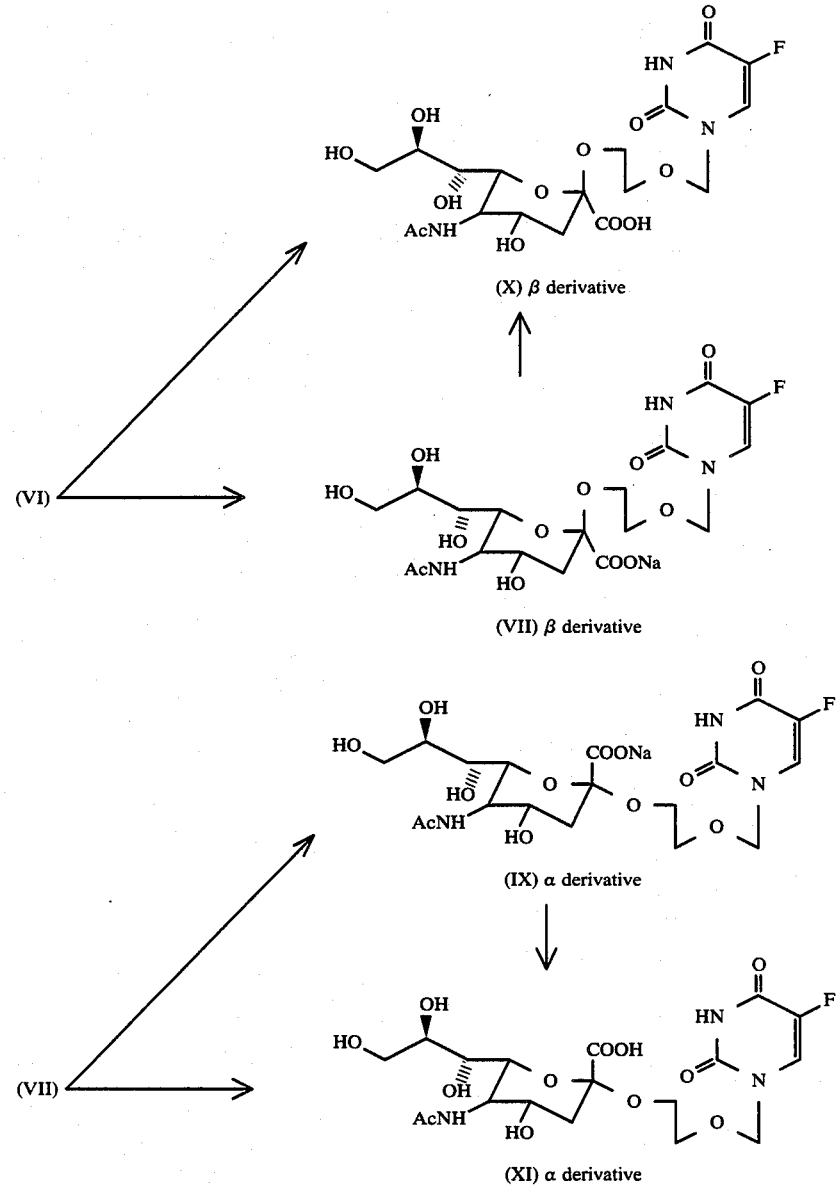

The compounds (II) and (III) described above are known compounds. The compound (II) is synthesized by, for example, a method described in Kuhn: Chem. Ber., 99,611 (1966). On the other hand, compound (III) is obtained by, for example, a method described in Morris J. Robins: Can. J. Chem., 60, 547 (1982).

A mixture of novel compounds (IV) (β-derivative) and (V) (α-derivative) is obtained by the Koenigs Knorr reaction of compound (II) and (III). The Koenigs Knorr reaction can be carried out in the presence of HgBr$_2$, Hg(CN)$_2$ or a mixture thereof, or in the presence of CF$_3$SO$_3$Ag (Silver trifluoromethane sulfonate). The reaction may preferably be carried out in the presence of CF$_3$SO$_3$Ag because CF$_3$SO$_3$Ag tends to make the total yield of the compounds (IV) and (V) higher than HgBr$_2$ and the like.

Further, said reaction carried out in the presence of CF$_3$SO$_3$Ag may preferably be carried out in a solvent such as tetrahydrofuran, acetonitrile, methylene chloride or the like at temperatures of room temperature to −50° C. for about 5 to 60 minutes. In particular, it is prefered that the reaction time be about 20 minutes and the solvent be tetrahydrofuran. Then novel compounds (IV) (β-devivative and (V) (α-derivative) of the present invention can be separated and purified by silica gel column chromatography of the product obtained above.

Further, novel compound (VI) (β-derivative) can be obtained by transesterification of the compound (IV) using sodium methoxyde in methanol. Similarly, novel compound (VII) (α-derivative) of the present invention can be obtained from the compound (V).

Then the compounds (VIII) (β-derivative) and (IX) (α-derivative) can be obtained by hydrolyzing the compounds (VI) and (VII) in a sodium hydroxide solution. The free acid type compounds (X) (β-derivative) and (XI) (α-derivative) can be obtained by acidifying aqueous solutions of compounds (VIII) and (IX) or hydrolyzing the componds (VI) and (VII) in a sodium hydroxide solution and acidfying it.

The preparation method of the present compounds shown by the serial chemical formulas will be shown concretely in the following examples.

According to the present invention, the compounds having the formula (I) have an excellent activity capable of adjusting the strength of the immune system. Activity capable of adjusting the strength of the immune system could be ascertained by the following method.

The function against the activation of mouse spleen lymphocyte by Con A:

As a T cell is non-specifically activated by Con A, glycoside of the present invention was added to the reaction and then, the function thereof was studied. That is, Con A and a compound having the formula (I), for example, the compound prepared in Examples will be shown afterward, were respectively added to the spleen lymphocyte (SPC) which was taken from BALB/C mouse and the mixture was cultured for 20 hours or so on the micro plate with 5% $CO_2$ added to the mixture at 37° C. Thymidine labeled with tritium was added to the mixture obtained and then SPC was collected further after culturing the mixture at 37° C. for 10 hours or so. The amount of $^3$H-thymidine taken in SPC was determined by using a scintillation counter.

Relative to a compound having the formula (I), promotion and reinforcement on $^3$H-thymidine taken in was observed, and an improvement in the function against the activation of T-cell by Con A was also observed.

The function against the production of immunoglobulin of mouse spleen lymphocyte:

As for N-substituted neuraminic acid derivatives of the present invention which were indicated in the activation of T-cell in the previous experiment, the function against the production of immunoglobulin was studied further by measuring the number of plaque-forming cells (PFC).

At first, red blood cells of sheep and one of the compounds having the formula (I), for example, the compound prepared in Examples will be shown afterward, was added to SPC and the mixture was cultured at 37° C. for 5 days. SRBC and complement were added again to sensitized SPC thus obtained. The number of PFC was counted after said mixture was cultured in a Cunningham chamber at the temperature of 37° C. for 3 to 12 hours.

Since decrease in the number of PFC was observed and the cell viability was the same as in the control, it was ascertained that repression against production of immunoglobulin was strengthened.

The compounds of the present invention showed an excellent activity in the two kinds of examination identified above. According to this fact, it was considered that the production of immunoglobulin was repressed by activating suppressor T cell.

So far, lowering of the function of suppressor T cell has been observed in autoimmune diseases such as collagen disease. Accordingly, N-substituted neuraminic acid derivatives of the present invention having activation function to suppressor T cell are expected to be effective in clinical applications as an agent for adjusting the strength of the immune system.

The present invention will now be illustrated by referring to the following nonlimitative examples.

EXAMPLE 1

Preparation method of compounds (IV) and (V):

120 ml of anhydrous tetrahydrofuran solution containing 2.54 g (12.44 mmol) of the compound (III) was added with 50 ml anhydrous acetonitrile solution containing 1.12 g (4.44 mmol) of mercuric cyanide and 2.24 g (6.21 mmol) of mercuric bromide, added 7.74 g of molecular sieves 4A powder and stirred at room temperature for 1 hour.

Then 35 ml of anhydrous acetonitrile solution containing 4.64 g (9.10 mmol) of the compound (II) was added to the resulting mixture obtained above and stirred at room temperature for 46 hours.

After the reaction suspension was neutralized with amberlist ® A-21 and filtrated. The resulting filtrate was distilled under reduced pressure, and the residue was dissolved in ethyl acetate, absorbed on 10 g of silicagel (Wakogel C-300) and distilled off under reduced pressure then separated to a number of fragments by the columnchromatography [solid phase: silicagel (Wakogel C-300) 100 g, eluting solvent: chloroform/methanol=30/1]. Raw materials were recovered from the first fragment and a mixture of compounds (IV) and (V), object products, were obtained. After the mixture was separated into fragments by the columnchromatography [solid phase: silicagel (Wakogel C-300), eluting solvent: toluene/methanol=10/1], solvent of two fragments were distilled off respectively, residue was dissolved in water and subjected to freeze drying. Whereupon 1.82 g (yield: 29.6%) of compound (IV) ($\beta$-derivative) and 1.87 g (yield: 30.4%) of compound (V) ($\alpha$-derivative) were obtained as pure colorless amorphous crystals. The total yield of compounds (IV) and (V) was 60.0%.

| Physical Properties of compound (IV) | | |
|---|---|---|
| Decomposition point | 100–109° C. | |
| Elemental analysis | $C_{27}H_{36}FN_3O_{16} \cdot \frac{3}{5} H_2O$ | MW=688.42 |
| Calculation | C: 47.11 | H: 5.45 |
| | N: 6.10 | |
| Found | C: 47.15 | H: 5.41 |
| | N: 5.80 | |
| $IR\nu_{max}^{KBr}$ cm$^{-1}$: | 3400(—NH—), 1720(—CO—O—) | |
| | 1670($\nu$C=O amide I), | |
| | 1550($\nu$C=O amide II), | |
| | 1230(C—O—C) | |
| $^1$H—NMR$_{400}^{ppm}$ MHz | (CDCl$_3$) | |
| | 1.894, 2.027, 2.035, 2.063, | |
| | 2.149 (15H, all S, CH$_3$CO—X5) | |
| | 2.342 (1H, dd, J=13.1Hz, J=4.9Hz, 3-Heq) | |
| | 3.802 (3H, S, —COOCH$_3$) | |
| | 3.539; 3.656 (2H, m; m,—OCH$_2$CH$_2$—O—) | |
| | 3.716; 3.907 (2H, m; m,—OCH$_2$CH$_2$—O—) | |
| | 4.780 (1H, d, J=10.7Hz, | |
| | $\begin{array}{c} O \quad H \\ \diagdown \diagup \\ C \\ \diagup \diagdown \\ N \quad H \end{array}$ ) | |
| | 5.603 (1H, d, J=10.7Hz, | |
| | $\begin{array}{c} O \quad H \\ \diagdown \diagup \\ C \\ \diagup \diagdown \\ N \quad H \end{array}$ ) | |
| | 5.107–5.174 (1H, m, 4-H) | |
| | 7.457 (1H, d, J=5.2Hz, pyrimidine-6-H) | |
| $[\alpha]_D^{24}$ - 5.75° | (C=1, AcOEt) | |

| Physical properties of compound (V) | | |
|---|---|---|
| Decomposition point | 94–105° C. | |
| Elemental analysis | $C_{27}H_{36}FN_3O_{16} \cdot \frac{11}{10} H_2O$ | MW=697.43 |

|  |  |  |
|---|---|---|
| Calculation | C: 46.50 | H: 5.52 |
|  | N: 6.03 |  |
| Found | C: 46.51 | H: 5.24 |
|  | N: 5.90 |  |
| IR$\nu_{max}^{KBr}$ cm$^{-1}$: | 3350 (—NH—), 1720 (—CO—O—), |  |
|  | 1670 ($\nu$C=O, amide I), |  |
|  | 1550 ($\nu$C=O, amide II), |  |
|  | 1220 (C—O—C) |  |
| $^1$H—NMR$_{400}^{ppm}$ MHz | (CDCl$_3$) |  |
|  | 1.888, 2.040, 2.148, |  |
|  | 2.153 (15H, all S, CH$_3$CO—X5) |  |
|  | 2.578 (1H, dd, J=12.7Hz, J=4.8Hz, 3-Heq) |  |
|  | 3.808 (3H,S, —COOC$\underline{H}$$_3$) |  |
|  | 3.475; 3.906 (2H, m; m,—OC$\underline{H}_2$CH$_2$—O—) |  |
|  | 3.737 (2H, m, —OCH$_2$C$\underline{H}_2$—O—) |  |
|  | 5.173 (1H, d, J=10.7Hz |  |
|  | $\begin{matrix} O & \underline{H} \\ \diagdown & \diagup \\ & C \\ \diagup & \diagdown \\ N & H \end{matrix}$ ) |  |
|  | 5.210 (1H, d, J=10.7Hz |  |
|  | $\begin{matrix} O & H \\ \diagdown & \diagup \\ & C \\ \diagup & \diagdown \\ N & \underline{H} \end{matrix}$ ) |  |
|  | 4.800–4.903 (1H, m, 4-H) |  |
|  | 7.530 (1H, d, J=5.2Hz, pyrimidine-6-H) |  |
| $[\alpha]_D^{24}$ - 8.08° | (C=1, AcOEt) |  |

EXAMPLE 2

Preparation method of compounds (IV) and (V) (2):

70 ml of anhydrous tetrahydrofuran solution containing 1.54 g (7.55 mmol) of compound (III) and 2.96 g (5.81 mmol) of compound (II) was added with 4.61 g of molecular sieves 4A powder and stirred at room temperature for 30 minutes. Then the obtained mixture solution was cooled to −15° to −20° C., added with 8 ml of anhydrous tetrahydroruran solution containing 2.09 g (8.13 mmol) of silver trifuluoromethane sulfonate and stirred for 20 minutes.

After filtration of the reaction suspension obtained and distilling off of the solvent in the resulting filtrate under reduced pressure, residue was dissolved in 200 ml of ehtyl acetate, washed with water saturated with sodium chloride and water saturated sodium hydrogencarbonate and dried with Na$_2$SO$_4$. Then 4.23 g of residue was obtained by filtrating the drying agent and distilling off the solvent under reduced pressure. 4.23 g of the residue was dissolved in ehtyl acetate and separated into fractions by the silicagel chromatography [solid phase: silicagel (Wakogel C-300) 423 g, eluting solvent: toluene/methanol=10/1]. First fragment (mixture of raw materials and compound (IV)) and second fragment (containing compound (V)) were obtained.

After distilling off of a solvent, residue of the first fraction was separated to fractions by column-chromatography [solid phase: silicagel (Wakogel C-300), eluting solvent: chloroform/methanol=40/1]. Solvent was distilled off from a fragment containing compound (IV), a residue was dissolved in water and subjected to freeze drying. Whereupon 0.77 g (yield: 19.6%) of compound (IV) ($\beta$-derivative) was obtained as a pure product. After distilling off of the solvent from the second fragment, the residue was dissolved in water and subjected to freeze drying, whereby 2.70 g (yield: 68.7%) of compound (V) ($\beta$derivative) was obtained as a pure product. The total yield of compounds (IV) and (V) was 88.3%.

EXAMPLE 3

Preparation of compound (VI):

420 mg (0.62 mmol) of compound (IV) obtained in examples 1 and 2 was dissloved in 100 ml of 0.01N sodium methoxid-methanol solution and stirred at room temperature for 1.5 hours. A reaction solution obtained was added with Dowex 50W-X8 H form, neutralized and filtrated. Then the resulting filtrate was concentrated and dried. The residue was subjected to column-chromatography [solid phase: Silicagel (Wakogel C-200), eluting solvent: chloroform/methanol=5/3]. The solvent was distilled off from a separated fragment, and the residue obtained was dissolved in water and subjected to freeze drying. Whereupon, 270 mg (yield: 86%) of compound (VI) ($\beta$-derivative) was obtained as a pure colorless amorphous crystal.

| Physical properties of the product | | |
|---|---|---|
| Decomposition point | 138–142° C. | |
| Elemental analysis | C$_{19}$H$_{28}$FN$_3$O$_{12}$·$\frac{7}{2}$ H$_2$O | MW = 572.51 |
| Calculation | C: 39.86 | H: 6.16 |
|  | N: 7.34 |  |
| Found | C: 39.62 | H: 5.90 |
|  | N: 7.13 |  |
| IR$\nu_{max}^{KBr}$ cm$^{-1}$: | 3400 (—NH—, —OH—), |  |
|  | 1710 (—CO—O—), |  |
|  | 1670 ($\nu$C=O amide I), |  |
|  | 1560 ($\nu$C=O amide II) |  |
| $^1$H—NMR$_{400}^{ppm}$ MHz | (CDCl$_3$ + D$_2$O) |  |
|  | 1.758 (1H, dd, J=12.4Hz, J=11.9Hz, 3-Hax) |  |
|  | 2.035 (3H, S, CH$_3$CONH—) |  |
|  | 2.347 (1H, dd, J=12.4Hz, J=4.8Hz, 3-Heq) |  |
|  | 3.320–4.080 (13H, m, sialyl-H, |  |
|  | —CH$_2$CH$_2$—O—) |  |
|  | 3.823 (3H, S, COOC$\underline{H}_3$) |  |
|  | 7.940 (1H, d, J=5.4Hz, pyrimidine-6-H) |  |
| $[\alpha]_D^{19.5}$ −17.9° | (C=1, DMF) |  |

EXAMPLE 4

Preparation of compound (VII):

In accordance with the procedure of example 3 but using compound (V) obtained in examples 1 and 2 in place of compound (IV), there was obtained 221 mg (yield: 80%) of compound (VII) ($\alpha$-derivative).

| Physical properties of the product | | |
|---|---|---|
| Decomposition point | 147–150° C. | |
| Elemental analysis | C$_{19}$H$_{28}$FN$_3$O$_{12}$·$\frac{19}{10}$ H$_2$O | MW=543.69 |
| Calculation | C: 41.97 | H: 5.90 |
|  | N: 7.73 |  |
| Found | C: 41.77 | H: 5.72 |
|  | N: 7.59 |  |
| IR$\nu_{max}^{KBr}$ cm$^{-1}$: | 3400 (—NH—, —OH—), |  |
|  | 1710 (—CO—O—), |  |
|  | 1670 ($\nu$C=O, amide I), |  |
|  | 1560 ($\nu$C=O amide II) |  |
| $^1$H—NMR$_{400}^{ppm}$ MHz | (CDCl$_3$ + D$_2$O) |  |

| Physical properties of the product | |
|---|---|
| | 1.758 (1H, dd, J=12.4Hz, J=11.1Hz, 3-Hax) |
| | 2.010 (3H, S, CH₃CONH—) |
| | 2.637 (1H, dd, J=12.4Hz, J=4.5Hz, 3-Heq) |
| | 3.484–3.972 (13H, m, sialyl-H, —CH₂CH₂—O—) |
| | 3.836 (3H, S, —COOCH₃) |
| | 7.906 (1H, d, J=5.3Hz, pyrimidine-6-H) |
| $[\alpha]_D^{19.5}$ -33.4° | (C=1, DMF) |

EXAMPLE 5

Preparation of compound (VIII):

650 mg (1.28 mmol) of compound (VI) obtained in example 3 was added with 2 ml of water and suspended, then added with 2 ml of 1N sodium hydroxide aqueous solution and stirred at room temperature for 20 minutes. Then 1N sodium hydroxide aqueous solution was added to the obtained mixture until the pH of the reaction mixture was between from 10 and 11 and the resulting mixture was stirred for 5 minutes. The reaction mixture was added with Amberlite® IRC-50, adjusted in its pH to between 5 and 6 and filtrated. Then the obtained filtrate was subjected to freeze drying and 636 mg (yield: 96.1%) of compound (VIII) was obtained as a colorless amorphous crystal.

| Physical properties of the product | | |
|---|---|---|
| Decomposition point | 196–201° C. | |
| Elemental analysis | $C_{18}H_{25}FN_3NaO_{12} \cdot \frac{14}{5} H_2O$ | MW = 567.86 |
| Calculation | C: 38.07 | H: 5.43 |
| | N: 7.40 | |
| Found | C: 37.80 | H: 5.25 |
| | N: 7.20 | |
| $IR\nu_{max}^{KBr}$ cm⁻¹: | 3400 (—NH, —OH), | |
| | 1700, 1670 (νC=O amide I) | |
| | 1610 (—COO⊖), | |
| | 1560 (νC=O amide II). | |
| $[\alpha]_D^{19.5}$ −15.5° | (C=1, H₂O) | |
| ¹H—NMR$_{400}^{ppm}$MHz | (DMSO-d₆, t-BuOH) | |
| | 1.465 (1H, t, J=11.9Hz, 3-Hax) | |
| | 1.871 (3H, S, CH₃CONH—) | |
| | 2.083 (1H, dd, J=11.9Hz, 4.5Hz, 3-Heq) | |
| | 3.331–3.669 | |
| | (10H, m, sialyl-H, —O—CH₂CH₂—O—) | |
| | 3.808 (1H, m, 4H) | |
| | 5.052 (1H, d, J=10.3Hz,  ) | |
| | 5.090 (1H, d, J=10.3Hz,  ) | |
| | 5.276 (1H, —OH) | |
| | 8.113 (1H, s, J=6.6Hz, primidine-6'H) | |
| | 8.245 (1H, d, J=7.3Hz, CH₃CONH—) | |

EXAMPLE 6

Preparation of compound (IX):

In accordance with the procedure of example 5 but using 372 mg (0.73 mmol) of compound (VII) obtained in example (4) in place of compound (VI) and using 1.5 ml of 1 N sodium hydroxide aqueous solution, 373 mg (yield: 98.6%) of compound (IX) was obtained.

| Physical properties of the product | | |
|---|---|---|
| Decomposition point | 178–183° C. | |
| Elemental analysis | $C_{18}H_{25}FN_3NaO_{12} \cdot 4H_2O$ | MW = 589.48 |
| Calculation | C: 36.68 | H: 5.64 |
| | N: 7.13 | |
| Found | C: 36.39 | H: 5.51 |
| | N: 6.95 | |
| $IR\nu_{max}^{KBr}$ cm⁻¹: | 3400 (—NH, —OH), | |
| | 1700, 1670 (νC=O amide I) | |
| | 1610 (—COO⊖), | |
| | 1560 (νC=O, amide II) | |
| $[\alpha]_D^{19.5}$ −4.5° | (C=1, H₂O) | |
| ¹H—NMR$_{400}^{ppm}$Hz | (DMSO-d₆, t-BuOH) | |
| | 1.242 (1H, t, J=11.7Hz, 3-Hax) | |
| | 1.888 (3H, S, CH₃CONH) | |
| | 2.650 (1H, dd, J=11.7Hz, 4.6Hz, 3-Heq) | |
| | 3.18–3.58 (10H, m, sialyl-H, —O—CH₂CH₂—O—) | |
| | 3.725 (1H, m, 4-H) | |
| | 4.793 (1H, m, —OH) | |
| | 5.035 (2H, S, —OCH₂N⟨ ) | |
| | 5.235 (1H, S, —OH) | |
| | 6.338 (1H, S, —OH) | |
| | 8.118 (2H, d, J=6.4Hz, Pyrimidine-6'H) | |
| | 8.439 (1H, d, J=6.1Hz, CH₃CONH—) | |

EXAMPLE 7

Preparation of compound (X) (1):

A solution of 100 mg (1.28 mmol) of compound (VIII) obtained in example 5 and 30 ml of distilled water was added with about 3 ml of Dowex 50W-X8 (H form) and stirred at room temperature for 1 hour. The pH of the resulting solution was 4.

The filtrate obtained by filtrating the reaction mixture was subjected to freeze drying and there was obtained 84 mg (yield: 89.2%) of compound (X) as a colorless amorphous crystal.

| Physical properties of the product | | |
|---|---|---|
| Decomposition point | 138–148° C. | |
| Elemental analysis | $C_{18}H_{26}FN_3O_{12} \cdot \frac{11}{10} H_2O$ | MW=515.25 |
| Calculation | C: 41.96 | H: 5.52 |
| | N: 8.16 | |
| Found | C: 41.70 | H: 5.20 |
| | N: 8.08 | |
| $IR\nu_{max}^{KBr}$ cm⁻¹: | 3400 (—OH, —NH—), | |
| | 1700 (—COOH), 1680 (—NHCO—) | |
| ¹H—NMR$_{400}^{ppm}$ MHz | (DMSO—d₆) | |
| | 1.620 (1H, t, J=12.5Hz, 3-Hax), | |

-continued

| Physical properties of the product | |
|---|---|
| | 1.961 (3H, S, C$\underline{H}_3$CONH—) |
| | 2.257 (1H, dd, J=12.5Hz, 4.5Hz, 3-Heq) |
| | 3.90–3.89 (1H, m, 4-H), |
| | 5.136 (2H, S, —OC$\underline{H}_2$N$\diagup\diagdown$ ) |
| | 7.972 (1H, d, J=6.0Hz, pyrimidine-6'H) |
| $[\alpha]_D^{19.5}$ - 16.8° | (C=1, H$_2$O) |

EXAMPLE 8

Preparation of compound (XI) (1):

In accordance with the procedure of example 7 but using 102 mg (0.20 mmol) of compound (IX) obtained in example 6 in place of compound (VIII), there was obtained 90.4 mg (yield: 92.4%) of compound (XI).

| Physical properties of the compound (XI) | | |
|---|---|---|
| Decomposition point | 123–128° C. | |
| Elemental analysis | C$_{18}$H$_{26}$FN$_3$O$_{12}$.H$_2$O | MW=513.45 |
| Calculation | C: 42.11 | H: 3.70 |
| | N: 8.18 | |
| Found | C: 41.85 | H: 3.41 |
| | N: 8.10 | |
| IR$\nu_{max}^{KBr}$ cm$^{-1}$: | 3400 (—OH, —NH—), | |
| | 1700 (—COOH), 1680 (—NHCO—), | |
| $^1$H—NMR$_{400}^{ppm}$ MHz | (DMSO—d$_6$), | |
| | 1.572 (1H, t, J=12.2Hz, 3-Hax), | |
| | 1.953 (3H, S, C$\underline{H}_3$CONH—), | |
| | 2.655 (1H, dd, J=12.2Hz, 4.5Hz, 3-Heq), | |
| | 3.82–3.90 (1H, m, 4-H), | |
| | 5.124 (2H, S, —OC$\underline{H}_2$N$\diagup\diagdown$ ) | |
| | 7.975 (1H, d, J=6.0Hz, pyrimidine-6'H) | |
| $[\alpha]_D^{19.5}$ - 5.8° | (C=1, H$_2$O) | |

EXAMPLE 9

Preparation of compound (X) (2):

100 mg (0.196 mmol) of compound (VI) obtained in example 3 was dissolved in 2 ml of water and added with 0.2 ml of 1 N sodium hydroxide aqueous solution. After agitating at room temperature for 3 hours, the reaction mixture was added with Dowex 50W-X8 (H type), stirred for about 30 minutes, filtrated and washed with water. The filtrate and the washing solution were subjected to freeze drying and there was obtained 90 mg (yield: 93%) of the compound (X).

EXAMPLE 10

Preparation of compound (XI) (2):

In accordance with the precedure of example 9 but using compound (VII) obtained in example 4 in place of compound (VI), 88 mg (yield: 91%) of compound (XI) was obtained.

We claim:

1. A glycoside having the formula:

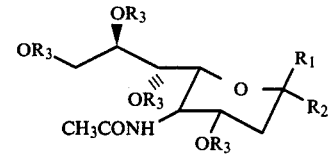

[I]

wherein R$_1$ is selected from the group consisting of

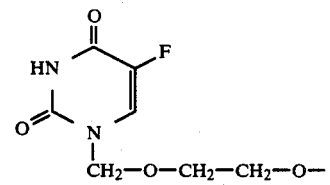

, methoxycarbonyl ethoxycarbonyl, the carboxyl group and the sodium, potassium or calcium salt of the carboxyl group: R$_2$ is methoxycarbonyl, ethoxycarbonyl, the carboxyl group or the salt of the carboxyl group when R$_1$ is

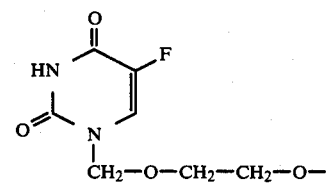

R$_2$ is

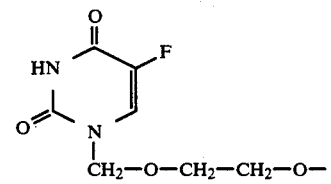

when R$_1$ is

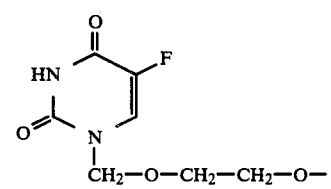

methoxycarbonyl, ethoxycarbonyl, the carboxyl group or the sodium, potassium or calcium salt of the carboxyl group; and R$_3$ is hydrogen or acetyl.

2. The glycoside of claim 1, wherein R$_1$ is

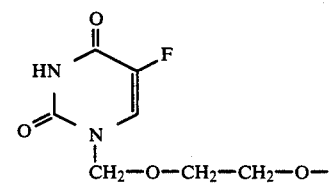

and $R_2$ is methoxycarbonyl, ethoxycarbonyl, the carboxyl group or the sodium, potassium or calcium salt of the carboxyl group.

3. The glycoside of claim 1, wherein $R_1$ is methoxcarbonyl, ethoxycarbonyl, the carboxyl group or the sodium, potassium or calcium salt of the carboxyl group and $R_2$ is

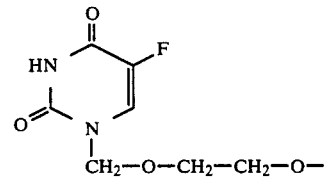

4. The glycoside of claim 1, wherein the alkoxycarbonyl group is methoxycarbonyl.

* * * * *